United States Patent [19] [11] 4,322,323
Capozza [45] Mar. 30, 1982

[54] ERODIBLE DEVICE COMPRISING SURFACTANT FOR MODIFYING THE RATE OF EROSION OF THE DEVICE

[75] Inventor: Richard C. Capozza, Paradise Valley, Ariz.

[73] Assignee: ALZA Corporation, Palo Alto, Calif.

[21] Appl. No.: 211,510

[22] Filed: Dec. 1, 1980

[51] Int. Cl.³ .............................. C08K 5/09
[52] U.S. Cl. .................... 424/78; 523/105; 524/612; 524/161; 524/156; 524/397; 424/19
[58] Field of Search ............ 260/18 R, 18 TN; 525/1, 525/3, 4, 5, 6; 528/370, 371, 403, 405, 406, 425

[56] References Cited
U.S. PATENT DOCUMENTS

3,301,824 1/1967 Hostettler ........................ 528/371
3,553,117 1/1971 Gutweiler ...................... 260/18 R
3,652,465 3/1972 Takakura ......................... 528/403
3,879,348 4/1975 Serini ............................... 528/371
4,066,747 1/1978 Capozza ........................... 528/403
4,079,038 3/1978 Choi ................................ 528/372
4,119,579 10/1978 Capozza ........................... 528/403
4,136,252 1/1979 Capozza ........................... 528/403
4,140,847 2/1979 Orvik .............................. 528/403
4,180,646 12/1979 Choi ................................ 528/153

Primary Examiner—Paul R. Michl

Attorney, Agent, or Firm—Paul L. Sabatine; Edward L. Mandell

[57] ABSTRACT

An erodible device is disclosed for delivering an agent to an environment of use. The device comprises (1) a structure sized and adapted for placement in an environment of use, the structure comprising a poly(orthoester) or a poly(orthocarbonate) having a repeating mer consisting of hydrocarbon radical and a symmetrical dioxycarbon unit of the general formula:

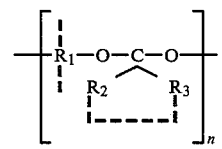

wherein $R_1$ is a multivalent hydrocarbon radical, $R_2$ and $R_3$ are hydrocarbon radicals with at least one of $R_2$ or $R_3$ bonded to the dioxycarbon through an oxygen covalent bond, (2) a beneficial agent, and (3) a surfactant erosion rate modifier. The devices are useful for delivering numerous agents to many environments. A composition also is disclosed comprising a poly(orthoester) or a poly(orthocarbonate), and a surfactant.

8 Claims, 10 Drawing Figures

ERODIBLE DEVICE COMPRISING SURFACTANT FOR MODIFYING THE RATE OF EROSION OF THE DEVICE

FIELD OF THE INVENTION

This invention pertains to delivery devices made of an erodible polymer with a surfactant in the device for modifying the rate of erosion.

BACKGROUND OF THE INVENTION

Commerce, science and medicine have long recognized the importance of delivery devices manufactured from erodible, agent release, rate controlling polymers. These devices are valuable because they contain a beneficial agent, that as the polymer erodes, is delivered at a controlled rate, and in an effective amount, to the environment of use. A major advance towards satisfying this recognition was met by the unique poly(orthoesters) and poly(orthocarbonates) disclosed in U.S. Pat. No. 4,180,646 issued to inventors Nam S. Choi and Jorge Heller. The new class of polymers disclosed in the patent comprised a polymeric backbone having a repeating unit comprising a hydrocarbon radical and a symmetrical dioxycarbon unit with a multiplicity of organic groups bonded thereto. These polymers have a controlled degree of erosion to innocuous products when in an aqueous or a biological environment. The polymers can be used for releasing a beneficial agent at a controlled rate to an environment of use.

While the above polymers are outstanding and represent a pioneering advancement in the polymer and the delivery arts, and while they are useful for dispensing numerous beneficial agents to an environment of use, there are instances where the rate of erosion of the polymers can be modified to produce a more preferred result. For example, when the polymers are used as implants in an animal environment of use, it may be therapeutically desirable to modify the rate of erosion the polymer. The rate is modified as a means for regulating the amount of drug released per unit time, by the implant over time. It will be appreciated by those versed in the present arts, that in view of the above presentation, if an erosion rate modifier is made available for poly(orthoesters) and poly(orthocarbonates), such a modifier would represent a valuable contribution and also useful improvement in the practicing arts.

OBJECTS OF THE INVENTION

Accordingly, it is an immediate object of this invention to provide novel and useful delivery devices with erosion rate modifiers for increasing the value of the devices in the practicing arts.

Another object of this invention is to provide an erosion rate modifier for poly(orthoester)-poly(orthocarbonate) polymers that aids in regulating the rate of erosion of the polymers over time.

Yet another object of the invention is to provide a device for delivering an agent that contains an erosion rate modifier that changes the length of time the device erodes and delivers an agent.

Another object of the invention is to provide a delivery device comprising an erosion rate modifier that effects the amount of agent released as the device erodes over time.

Yet another object of the invention is to provide an erodible device having an erosion rate modifier therein, that alters the rate of the erosion in aqueous and biological fluids over time.

Still another object of the invention is to provide a composition of matter comprising a poly(orthoester) or a poly(orthocarbonate) and a surfactant erosion rate modifier.

Yet still another object of the invention is to provide a bioerodible drug delivery device embracing a structure formed of a non-toxic bioerodible orthoester polymer, or a non-toxic bioerodible orthocarbonate polymer, a non-toxic surfactant polymer erosion rate modifier, and a drug.

Other objects, features and advantages of the present invention will become more apparent from the following detailed description of the invention and the appended claims defining the broad scope of the invention.

SUMMARY OF THE INVENTION

This invention concerns erodible delivery devices. The devices comprise a body formed of a polymeric backbone having a repeating unit of a hydrocarbon radical and symmetrical dioxycarbon unit with a multiplicity of organic groups bonded thereto. The polymers have a controlled degree of hydrophobicity with a corresponding controlled degree of erosion in an aqueous or a biological environment of use. The devices additionally contain a surfactant erosion rate modifier that cooperates with and interacts with polymers for regulating the rate of erosion of the polymers. A beneficial agent present in the devices is released at a controlled rate and in effective amounts as the polymers erode over time. The invention also concerns composition comprising the polymers and a surfactant.

DETAILED DESCRIPTION OF THE DRAWINGS

In the drawings, which are not drawn to scale, but are set forth to illustrate various embodiments of the invention, the figures are described as presented below.

Turning to FIG. 1, an agent delivery device provided by the invention is indicated by the numeral 10. Device 10, in this embodiment, comprises a body 11 that is shaped, sized, structured and adapted for placement in the environment of use. Device 10 has at least one surface 12 exposed to the environment that erodes in the presence of fluid found in the environment, and release an agent, not seen in FIG. 1, to the environment as the device erodes over a prolonged period of time.

FIG. 2 is a cross-sectional view of device 10, through 2—2 of FIG. 1. Device 10, in FIG. 2, comprises a body 11 formed of an erodible polymer 14 having distributed therein a surfactant erosion rate modifier 15 and a beneficial agent 16. Erodible polymer 14, is an agent release rate controlling material. Polymer 14 erodes at a controlled and continuous rate in the presence of rate modifier 15 and fluid in the environment, releasing agent 16 at a corresponding controlled and continuous rate.

Figure 1:
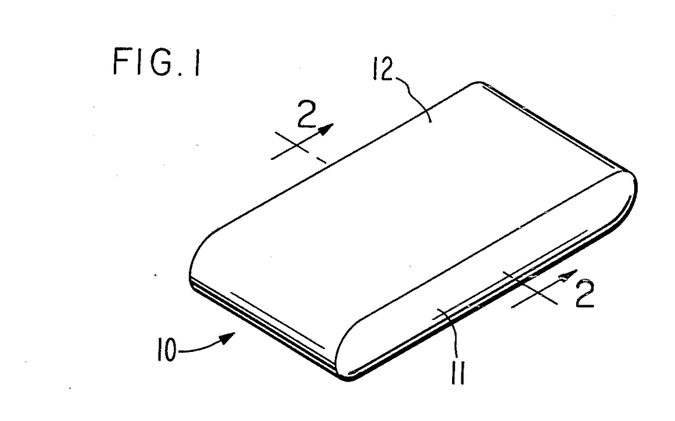
Figure 2:
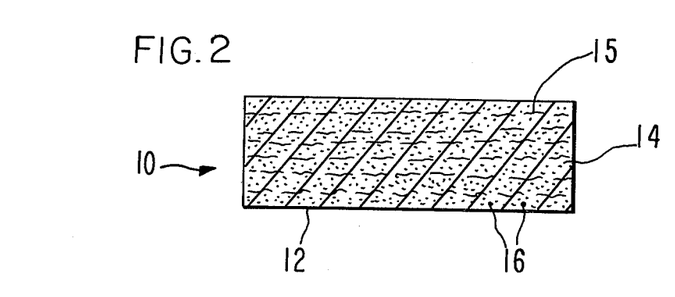
Figure 3:
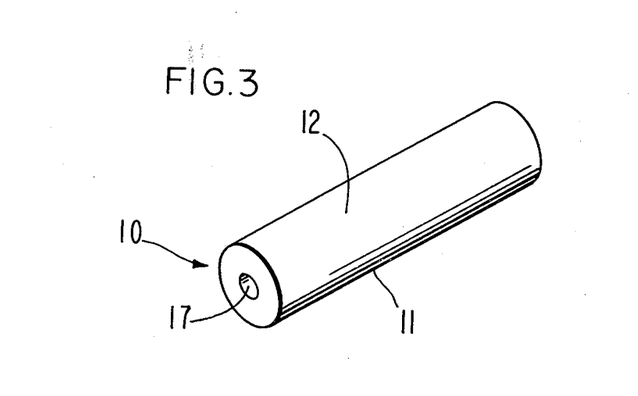
FIG. 3 is a view of an agent dispensing device 10 provided by the invention and manufactured in the shape of an implant for use in a biological environment. Device 10 comprises a body 11, formed of a bioerodible agent release rate controlling material having surfaces 12 and 17 for releasing an agent, not shown, to the environment over a prolonged period of time. The agent in the implant is a drug, and the biological environment is an animal, including a human.

While FIGS. 1 through 3 are illustrative of various erodible devices that can be made according to the invention, it is to be understood these devices are not limiting, as the devices can take a wide variety of shapes, sizes and forms adapted for delivering agents to different environments of use. For example, the devices include buccal, nasal, vaginal, ano-rectal, artifical gland, cervical, intrauterine, ocular, arterial, dermal, ear, and like biological environments. The devices also can be structured and adapted for delivering an active agent in streams, aquariums, fields, factories, reservoirs, laboratory facilities, hot houses, transportation means, naval means, hospitals, clinics, vetrinary clinics, nursing homes, chemical reactions, and other environments of use.

DETAILED DESCRIPTION OF THE INVENTION

The erodible poly(orthoesters) and erodible poly(orthocarbonates) useful for manufacturing the devices of the invention are represented by erodible release rate controlling polymers of the formula:

wherein, $R_1$ is a number selected from the group consisting of divalent, trivalent and tetravalent radicals consisting of alkylene of 1 to 10 carbons; alkenylene of 2 to 10 carbons, alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, alkenyl of 2 to 7 carbons, and an alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, an alkenyl of 2 to 7 carbons, and an alkylene of 1 to 7 carbons; arylene of 6 to 12 carbons; arylene of 6 to 12 carbons substituted with an alkyl of 1 to 7 carbons, an alkoxy of 1 to 7 carbons, and an alkenyl of 2 to 7 carbons; $R_2$ and $R_3$ are selected from the group consisting of alkyl of 1 to 7 carbons; alkenyl of 2 to 7 carbons; alkoxy of 1 to 7 carbons; alkylene of 1 to 7 carbons; alkenylene of 2 to 7 carbons; alkyloxy of 1 to 7 carbons; alkenyloxy of 2 to 7 carbons; alkyleneoxy of 1 to 7 carbons; alkenyleneoxy of 2 to 7 carbons; aryloxy of 6 to 12 carbons; aralkyleneoxy of 8 to 12 carbons; aralkenyleneoxy of 8 to 12 carbons; oxa; $OR_1O$ wherein $R_1$ is as defined above; a heterocyclic ring of 5 to 8 carbons and oxygen atoms formed when $R_2$ and $R_3$ are taken together; a heterocyclic ring of 5 to 8 carbons and oxygen atoms substituted with an alkyl of 1 to 7 carbons, an alkoxy of 1 to 7 carbons, and an alkenyl of 2 to 7 carbons formed when $R_2$ and $R_3$ are taken together; a fused polycyclic ring of 8 to 12 carbon and oxygen atoms formed when $R_2$ and $R_3$ are taken together, a fused polycyclic of 8 to 12 carbon and oxygen atoms substituted with an alkyl of 1 to 7 carbons, an alkoxy of 1 to 7 carbons and an alkenyl of 2 to 7 carbons; wherein at least one of $R_2$ and $R_3$ is selected from the group consisting of alkoxy, alkenyloxy and $OR_1O$; and when $R_2$ and $R_3$ are independently alkoxy and alkenyloxy and the other member of said $R_2$ and $R_3$ is selected from the group consisting of alkyl, alkenyl, alkoxy, alkenyloxy, alkylene, alkenylene, alkyleneoxy, and oxa; and when $R_2$ and $R_3$ are taken together, a member selected from the group of heterocyclic and fused polycyclic rings; and n is greater than 10, preferably 10 to $10^6$.

The term alkylene used in this specification and the accompanying claims denotes a straight or branched divalent, trivalent or tetravalent alkylene radical of 1 to 10 carbon atoms such as 1,2-ethylene; 1,3-propylene; 1,2-propylene; 1,4-butylene; 1,5-pentylene; 1,6-hexylene; 1,2,5-hexylene; 1, 3,6-hexylene; 1,7-heptytene; 2-methyl-1,7-heptylene; 1,8-octylene; and the like.

The term alkenylene denotes an unsaturated or branched chained multivalent radical having 2 to 10 carbon atoms such as 1,4-but-2-enylene; 1,6-hex-3-enylene; 1,7-hept-3-enylene; 1,8-oct-3-enylene; 1,9-non-3-enylene; 4-propyl-(1,6-hex-3-enylene); 5-methoxy-(1,6-hex-3-enylene); 2-propenyl-(1,6-hex-3-enylene); and the like.

The term cycloalkylene includes monocyclic, lower cycloalkylene radicals of 3 to 7 carbons such as cyclopropylene; cyclobutylene; cyclopentylene; cyclohexylene; and cycloheptylene. Similarly, the phrase cycloalkylene substituted with an alkyl of 1 to 7 carbons, an alkoxy of 1 to 7 carbons, an alkenyl of 2 to 7 carbons, or an alkylene of 1 to 10 carbons, includes substituted cycloalkylenes such as 2-methyl-1,3-cyclopropylene; 2-methyl-1,4-cyclopentylene; 2-methyl-1,6-cyclohexylene; 1-methylene-cyclohexylene; 1,6-dimethylene-cyclohexylene; 2-ethoxy-2,3-cyclopropylene; 5-butoxy-1,4-cyclopentylene; 2-methoxy-1,4-cyclohexylene; 2-propenyl-1,5-cyclopentylene; 2-isobutenyl-1,6-cyclohexylene; and the like.

Exemplary cycloalkenylene and cycloalkenylene substituted with an alkyl of 1 to 7 carbons, an alkoxy of 1 to 7 carbons, an alkenyl of 2 to 7 carbons, or an alkylene of 1 to 10 carbons include monocyclic cycloalkenylenes having 4 to 7 carbons as ring members, such as 1,4-cyclopent-2-enylene; 1,5-cyclopent-3-enylene; 1,6-cyclohex-2-enylene; 1,6-cyclohex-2-enylene; and the substituted rings such as 5-methyl-(1,4-cyclopent-2-enylene); 6-ethyl-(1,4-cyclohex-2-enylene); 6-ethoxy-(1,5-cyclohex-2-enylene); 2-propyl-(1,5-cyclohex-3-enylene); 2-methoxy-(1,4-cyclohex-2-enylene); 2-methoxy-(1,4-cyclohept-2-enylene); 1-methylene-(1,6-cyclohex-2-enylene); and the like.

The expressions arylene and arylene substituted with an alkyl of 1 to 7 carbons, an alkenyl of 2 to 7 carbons, an alkoxy of 1 to 7 carbons, or an alkylene of 1 to 10 carbons, include the benzenoid group of 6 to 12 carbons such phenylene, naphthalene, phenylalkylene, phenylalkenylene, 1,4-phenyldimethylene; 1,4-phenyldiethylene; 2-ethyl-1,4-phenyldimethylene; 2-methylene-1,4-phenyldimethylene; 2-3thyl-1,4-phenylimethylene; 2-meth-1,4-phenyldimethylene; 2-methoxy-1,4-phenyldimethylene, 2-propyl-1,4-phenyldiethylene; and the like.

The term alkyl embraces straight and branched chain alkyl radicals of 1 to 7 carbon atoms, such as methyl; ethyl; n-propyl; n-butyl; n-amyl; n-hexyl; n-heptyl; and the various positional isomers such as isopropyl; t-butyl; sec-butyl; isoamyl; isohexyl; t-heptyl; and the like.

The term alkenyl embraces straight and branched chain lower alkenyl groups of 2 to 7 carbons, such as 1-propenyl; 2-propenyl or alkyl; 1-butenyl; 2-butenyl;

1-pentenyl; 2-ethenyl; and the corresponding positional isomers such as 1-isobutenyl; 2-isobutenyl; 2-sec-butenyl; 2-methyl-1-butenyl; 2-methyl-2-pentenyl; 2,3-dimethyl-3-hexenyl; and the like.

The term alkoxy includes the straight and branched chain lower alkoxy groups, and the positional isomers thereof having 1 to 7 carbon atoms inclusive, for example, methoxy; ethoxy; propoxy; butoxy; n-pentoxy; n-hexoxy; isopropoxy; 2-butoxy; isobutoxy; 3-pentoxy; and the like.

The term alkenyloxy embraces straight and branched chain lower alkenyloxy groups and the positional isomers thereof having 2 to 7 carbon atoms, for example, ethenoxy; propenoxy; butenoxy; pentenoxy; hexenoxy; isopropenoxy; isobutenoxy; sec-butenoxy; 2-methyl-1-butenoxy; 2-methyl-2-butenoxy; 2,3-dimenthyl-3-butenoxy; and the like.

The term alkyleneoxy comprehends straight and branched chain alkyleneoxy radicals of 2 to 6 carbon atoms such as 1,3-propyleneoxy; 1,4-butyleneoxy; 1,5-pentyleneoxy; 1,6-hexyleneoxy; 2,2-dimethyl-1,4-butyleneoxy; and the like. Similarly, the term alkenyleneoxy comprehends 3 to 6 carbons, such as prop-1-enyleneoxy; 1,4-but-1-enyleneoxy; 1,4-but-2-enyleneoxy; 1,5-pent-1-enyleneoxy; 1,6-hex-1-enyleneoxy; and the like.

The expressions alkylenedioxy and alkenyldioxy include straight and branched chain radicals where the alkylene is of 2 to 6 carbons, and the alkenylene is of 3 to 6 carbons, such as for alkylenedioxy, propylenedioxy; butylenedioxy; pentylenedioxy; hexylenedioxy; and heptylenedioxy; and for alkenylenedioxyprop-1-enylenedioxy; 1,4-but-1-enylenedioxy; 1,4-but-2-enylenedioxy; 1,5-pent-1-enylenedioxy; 1,6-hex-1-enylenedioxy; and the like.

The terms alkylene and alkenylene used when $R_2$ and $R_3$ are taken together to form a ring in cooperation with the carbon of the carbon-oxygen polymer backbone, include an alkylene of 2 to 6 carbons, and an alkenylene of 3 to 6 carbons, such as the alkylenes, 1,2-ethylene; 1,3-propylene; 1,4-butylene; 1,5-pentylene; and 1,6-hexylene; and the alkenylenes 1,3-prop-1-enylene; 1,4-but-1-enylene; 1,4-but-2-enylene; 1,5-pent-1-enylene; 1,6-hex-2-enylene; and 1,7-hept-2-enylene.

The terms aryloxy, aralkyleneoxy, aralkenyleneoxy, aralkylenedioxy and aralkenylenedioxy indicate an aryl, of 6 to 12 carbons wherein the aryloxy is ar—o—, and the alkyleneoxy, alkenyleneoxy, alklenedioxy and alkenylenedioxy are as defined above and ar is preferably phenyl.

The phrase heterocyclic ring of 5 to 8 carbons for $R_2$ and $R_3$ define the ring formed when $R_2$ or $R_3$ is a bond, alkylene or alkenylene, and at least one of $R_2$ or $R_3$ is an alkyleneoxy, alkenyleneoxy, alkylenedioxy or alkenylenedioxy, with the terms as defined above, and when $R_2$ and $R_3$ are taken together, the ring is a member selected from the group consisting of dioxolanyl, dioxanyl, dioxepanyl dioxocanyl, furyl, dioxonanyl, tetrahydrofuranyl, dihydrofuranyl, pyranyl, ocanyl and oxepanyl.

The phrase fused polycyclic ring of 8 to 12 carbons with at least one or two oxygen atoms defines a substituent in which a heterocyclic and an aryl ring have two atoms in common; for example a member selected from group the consisting of benzfuryl; benzpyyranyl; 4,5-benz-1,3-dioxepanyl; 5,6-benz-1,3-dioxepanyl; 4,5-benz-1,3-dioxolanyl; 4,5-benz-1,3-dioxocanyl; 5,6-benz-1,3-dioxocanyl; 6,7-benz-1,3-dioxocanyl; 7,8-benz-1,3-dioxocanyl; and benz-1,3-dioxoanyl.

The poly(orthoesters), and the poly(orthocarbonates) described herein are known to the prior art in U.S. Pat. Nos. 4,093,709; 4,131,648; 4,138,344; and 4,180,646. These patents are issued to Nam. S. Choi and Jorge Heller and they are assigned to the ALZA Corporation of Palo Alto, Calif., the assignee of this invention.

The phrase erosion rate modifiers as used herein, denotes a surfactant that can assist in regulating the rate of erosion of the erodible polymers. The modifiers can increase the rate of erosion, or the modifiers can retard the rate of erosion over time. The modifiers suitable for the present purpose include surfactants that influence the electronics of the transition state formed during erosion of the polymer. The erosion of the polymer occurs by hydrolysis of the orthoester, or the orthocarbonate covalent bond in the polymer through a series of transient intermediates. The surfactant influences this electronic environment and concomitantly the rate of hydrolysis and the accompanying rate of formation of the transient species. For example, it has now been observed anionic surfactants have a rate accelerating effect on the rate of erosion, and cationic surfactants retard the rate of erosion. Nonionic surfactants have little effect, or a slight accelerating effect, because of their wetting properties.

Typical anionic surfactants generically include sulfated esters, sulfated amides, sulfated alcohols, sulfated ethers, sulfated carboxylic acids, sulfonated aromatic hydrocarbons, sulfonated aliphatic hydrocarbons, sulfonated esters, sulfonated amids, sulfonated ethers, acylated amino acids, acylated polypeptides, and the like.

Typical cationic surfactants generically include primary alkylammonium salts, secondary alkylammonium salts, tertiary alkylammonium salts, quaternary alkylammonium salts, acylated polyamines, salts of heterocyclic amines, benzyl ammonium salts, and the like.

Typical nonionic surfactants generically include esters of polyhydric alcohols, alkoxylated amines, esters of polyoxyalkylene glycols, ethers of polyoxyalkylene glycols, alkanolamine fatty acid condensates, tertiary acetylenic glycols, dialkyl polyoxyalkylene phosphates, and the like.

Examples of specific nonionic surfactants include dodecyl phenoxypolyethoxyethanol; isooctyl phenoxypolyethoxyethanol; oxyethylated straight chain alcohol; polyoxyethylene sorbitanmonolaurate; polyoxyethylene sorbitan-monole; polyoxyethylene stearate; poloxyethylene laurylalcohol, polyglycol ether or alkylphenol; and the like.

Examples of specific anionic surfactants include sodium oleate, sodium lauryl sulfate, sodium cetyl sulfate, sodium stearyl sulfate, sodium alkylbenzene sulfonate, dialkyl sulfosuccinate; dioctylester of sodium sulphosuccinic acid; sodium salt of alkylated aryl polyether sulfate; and the like.

Examples of specific cationic surfactants include lauryldimethyl benzylammonium chloride; diisobutylphenoxyethoxyethyldimethyl benzylammonium chloride; alkylclimethylbenzylammonium chloride; laurylisoquinolinium bromide, cetylethyldimethylammonium chloride; stearyldimethyl benzylammonium chloride; ethanolated kalkyl guanidine amine complex; and the like. The amount of surfactant, cationic, anionic and nonionic used for the present purpose is generally about 0.001% to 5% by weight based on the total weight of the device. The surfactants are known to the art in Surface Active Agents, by *Schwartz and Perry*, 1949, Interscience Publishers, New York; *Harry's Cosmeticology* edited by Wilkinson, 1973, Chemical Publishing Co., Inc. and, *Systemic Analysis of Surface Active Agents*, Rosen and Goldsmith, 1972, Wiley-Interscience, New York.

The term agent as used in the specification and accompanying claims includes pesticides, herbicides, germicides, biocides, algicides, rodenticides, fungicides, insecticides, plant growth promoters, plant growth inhibitors, preservatives, disinfectants, fertility inhibitors, fertility promoters, drugs and the like.

The term drug that can be administered according to the spirit of the invention include locally and systemically acting drugs. These drugs include a member selected from the group consisting of physiologically and pharmacologically acting drugs such as gastrointestinal administrable drugs, hypnotic, sedative, psychic energizer, tranquilizer, anticonvulsant, antiparkinson, muscle relaxant, analgesic, antipyretic, anti-inflammatory, anesthetic, antispasmodic, antimicrobial, antiviral, antiulcer, hormonal, sympathomimetic, diuertic, hypoglycemic, vitamin, contraceptive and opthalmic drugs. These beneficial drugs and their dose amounts for humans are known in Pharmacology in Medicine, by Drill and edited by DiPalma, 1965, published by McGraw-Hill, New York; in Pharmacological Basis of Therpeutics, by Goodman and Gilman, 4th Edition, 1970, MacMillan Co.; and in U.S. Pat. No. 3,997,404. The amount of agent, including drug, present in a device provided by the invention will be about 0.5% to 50% by weight per 100% by weight of polymer comprising the device. A more presently preferred range is about 10% to 40% weight by weight.

The devices of the invention can be manufactured by standard techniques. For example, the polymers with the agent and modifier mixed therewith can be extruded into filaments, spun into fibers, pressed into shaped articles, solvent film cast, doctor-bladed into thin films, coated by solvent evaporation, coated by using a fluidized bed, compression and transfer molded, and like methods of manufacture.

The devices can be a single matrix, a container with a reservoir therein, or, a number of layers. The devices can be made into various shapes for example, flat, square, round, tubular, disc, ring and the like. Also, the devices of the invention are sized, shaped and adapted for implantation, insertion, placement, depositing or spreading on the body, in the body, cavities and passageways of the body of an animal, which term embraces warm-blooded animals and humans. Standard procedures for processing the polymers, modifier and agent are described in *Plastic Encyclopedia*, Vol. 46, pages 62 to 70, 1969; and the patents cited supra.

The following examples are set forth as representative methods illustrative of the spirit of the present invention. These examples are not to be construed as limiting the scope of the invention, as these and other functionally equivalent methods will be readily apparent to those skilled in the subject art.

EXAMPLE 1

Twenty grams of tetracycline, the free base and previously dried at 60° C. for 8 hours in vacuum, was thoroughly mixed with 0.1% of the anionic surfactant dioctyl sodium sulfosuccinate, and the antibiotic surfactant mixture blended with 80 grams of poly (2,2-dioxo-cis/-trans-1,4-cyclohexane dimethylene tetrahydrofuran).

The polymer was previously heated to 100°–120° C., and the mixture mixed therein for 15 to 20 minutes to yield a homogenous composition.

Next, a 20 mil, 3"×3" film was pressed at 150° F. at 1500 psi for 5 minutes, followed by a 5-minute cooling period. Then, ellipsoidal devices 5×8 mm were punched from the cool film. The devices are useful as ocular inserts.

EXAMPLE 2

To 80 grams of a polymer of the formula, having a molecular weight of 44,000, where n is about 216, and which polymer was previously heated to 110°–120° C., was added 0.1 g of the neutral surfactant t-octyl-phenoxy-polyoxyethanol, and the polymer surfactant blended to give a homogenous composition. Then, with the composition at the raised temperature, 20 grams of dry tetracycline base was blended into the composition. The blending continued for 15 to 20 minutes.

Next, a 20 mil film was pressed at 150° F./15000 psi for 5 minutes, followed by a 10 minute cooling period. Ocular inserts of elipse shape, 5×8 mm were then punched from the film.

EXAMPLE 3

A composition, useful as a control for demonstrating the invention, was prepared by blending 20% tetracycline with the polymer illustrated in Example 2. Control inserts, 5×8 mm were prepared as described above.

EXAMPLES 4 to 7

Ocular dispensing devices comprising (a) 0.006% of benzalkonium chloride, 20% tetracycline, and 80% poly (2,2-dioxo-cis/trans-1,4-cyclohexane dimethylene tetrahydrofuran); (b) 0.05% of benzalkonium chloride, 20% of tetracycline, and 80% of poly(2,2-dioxo-cis/-trans-1,4-cyclohexane dimethylene tetrahydrofuran; (c) 0.1% triethanolamine, 20% tetracycline and 80% poly(2,2-dioxo-cis/trans-1,4-cyclohexande dimethylene tetrahydrofuran; and (d) 0.1% benzalkonium chloride, 20% tetracycline, and 20% poly(2,2-dioxo-cis/trans-1,4-cyclohexane dimethylene tetrahydrofuran, were manufactured according to the procedures described in Examples 1 to 3.

The drug release rates were determined for the devices in pH, 0.1 M phosphate buffer, and the drug release profiles presented as weight and percentage of drug released per hour. The release of the drug was at 37° C. The drug release rates were determined by the plot of UV absorbance at 356 nm vs. time in phosphate buffer. The results of the measurements are presented in Table 1. In the table, anionic surfactant indicates dioctyl sodium sulfosuccinate; neutral indicates t-octylphenoxypolyethox-ethanol, BzAC indicates benzalkonium chloride; and TEA indicates triethanolamine.

TABLE 1

| COMPOSITION | RATE OF DRUG RELEASE (μg/hr) | LIFETIME (hrs) |
|---|---|---|
| Control | 120 | 50 |
| 0.1% anionic surfactant | 140 | 50 |
| 0.1% neutral | 94 | 80 |
| 0.006% Cationic (BzAC) | 64 | 100 |
| 0.05% Cationic (BzAC) | 50 | 170 |
| 0.1% Cationic (TEA) | 37 | 115 |
| 0.1% Cationic (BzAC) | 28 | 240 |

Figure 4:
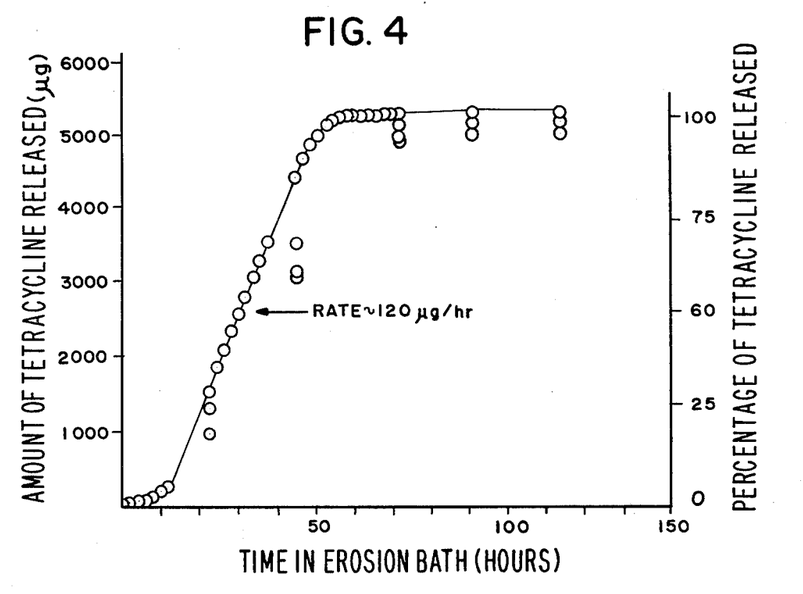
FIGS. 4 to 10 represent release rates for devices provided by the invention, and these Figures are described in detail later in the specification.
Figure 5:
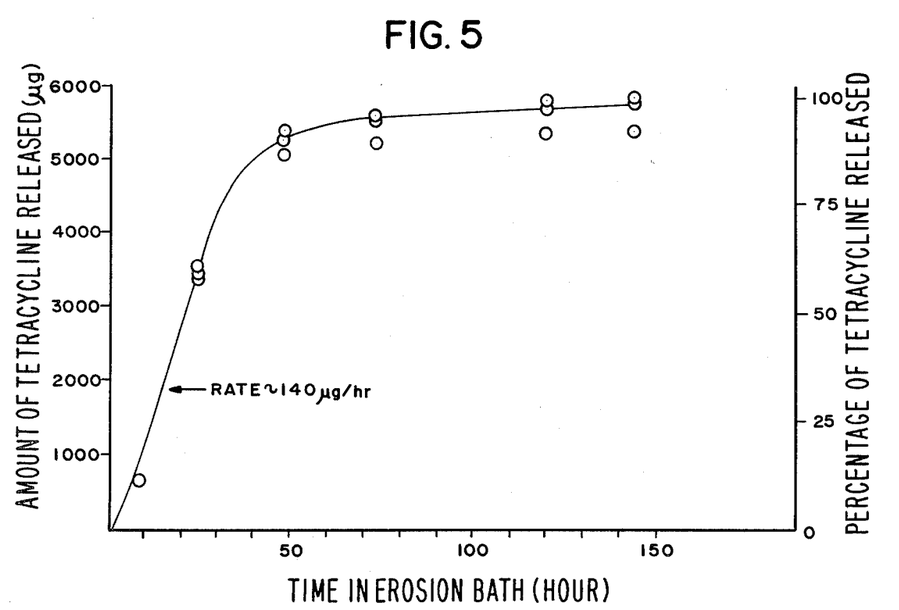
Figure 6:
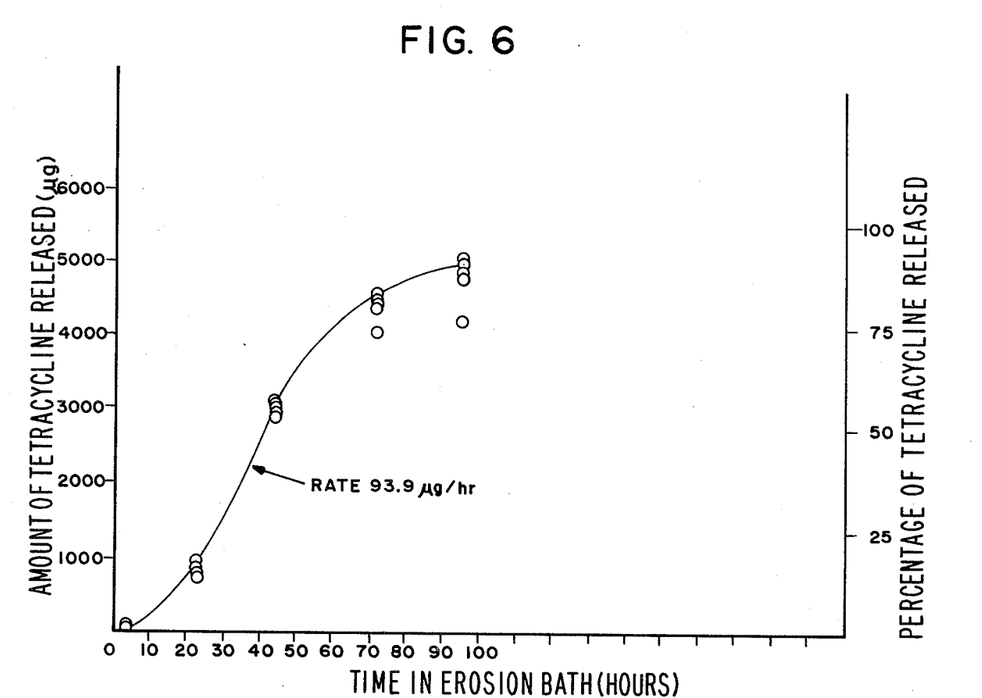
Figure 7:
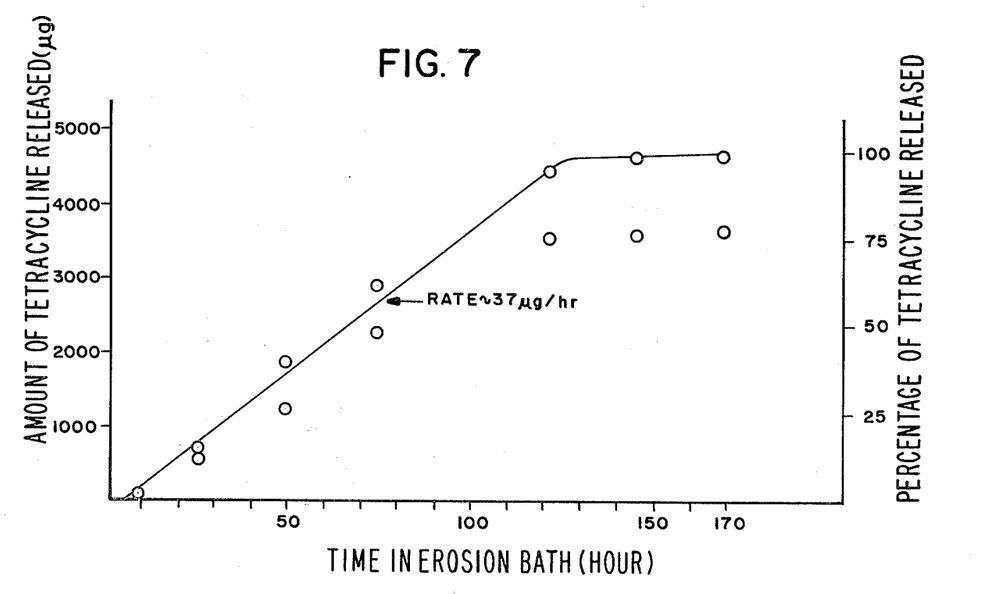
Figure 8:
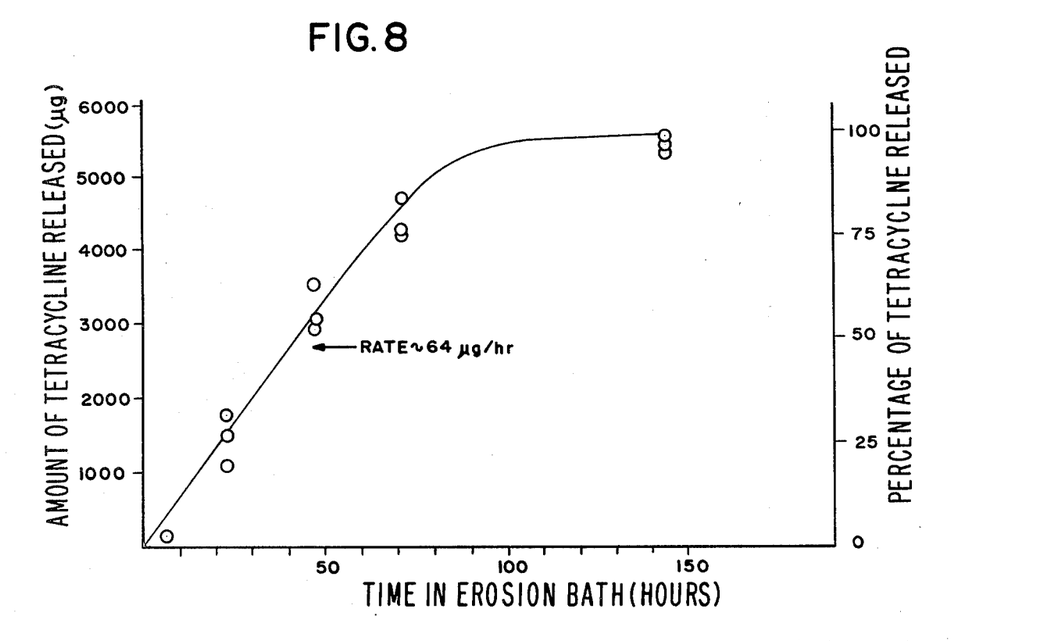
Figure 9:
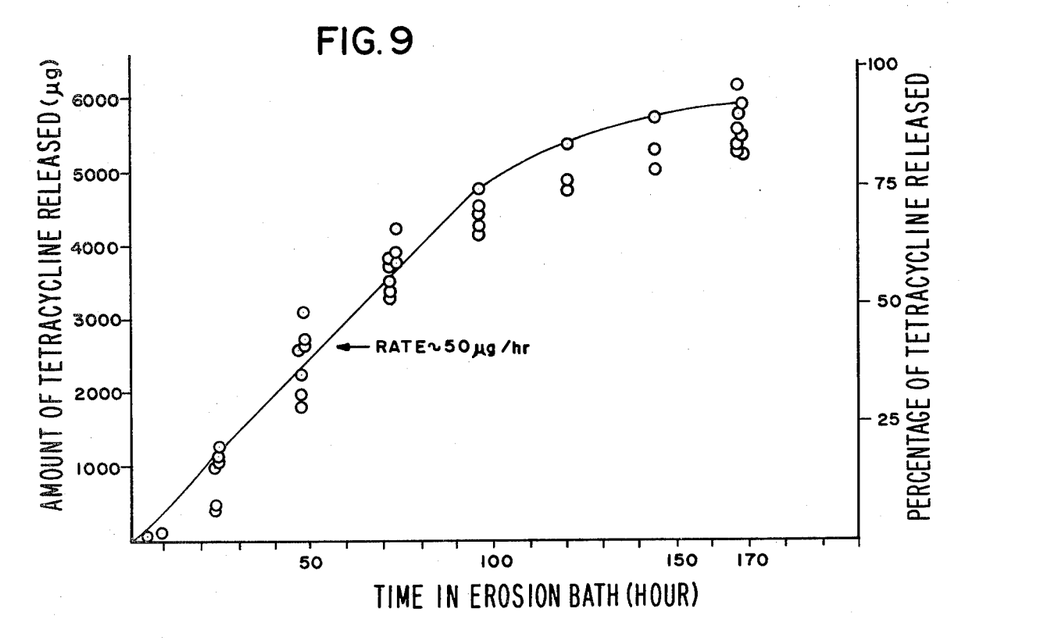
Figure 10:
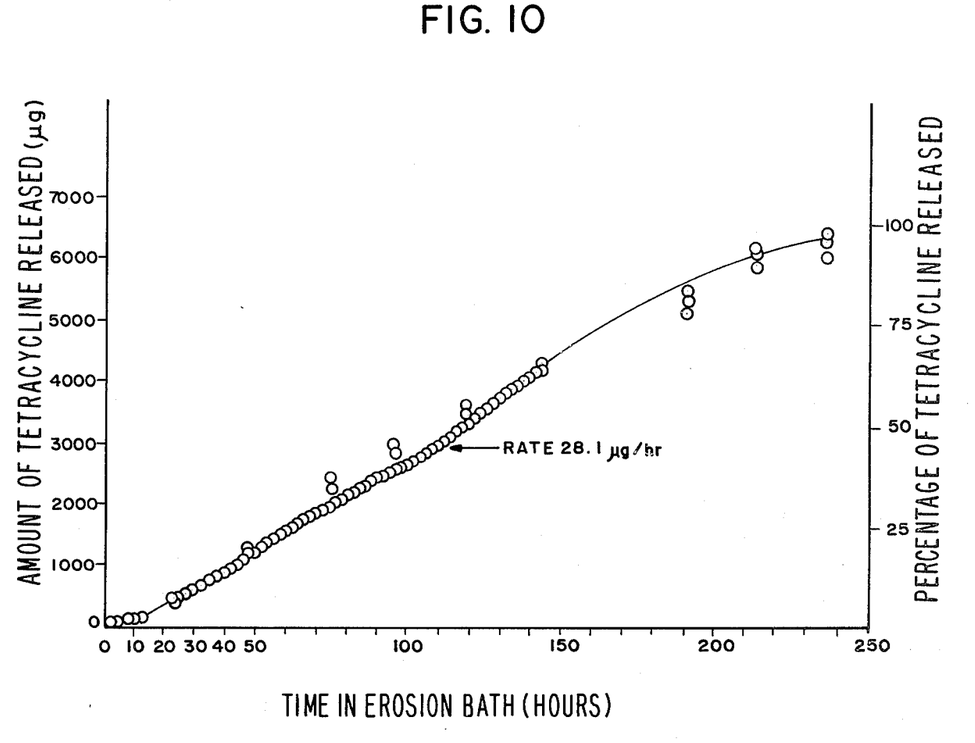

The results of the invention are further illustrated in FIGS. 4 to 10. In FIG. 4, the device comprised 20% tetracycline and 80% poly(2,2-dioxo-cis/trans-1,4-cyclohexane dimethylene tetrahydrofuran; in FIG. 5 the device comprised 20% tetracycline, 0.1% dioctyl sodium sulfosuccinate and 80% poly(2,2-dioxo-cis/-trans-1,4-cyclohexane dimethylene tetrahydrofuran); in FIG. 6 the device comprised 20% tetracycline, 0.1% t-octylphenoxy-polyethoxyethanol, and 80% poly(2,2-dioxo-cis/trans-1,4-cyclohexane dimenthylene tetrahydrofuran); in FIG. 7, the device comprised 20% tetracycline, 0.1% triethanolamine, and 80% poly(2,2-dioxo-cis/trans-1,4-cyclohexane dimethylene tetrahydrofuran); in FIG. 8 the device comprised 20% tetracycline, 0.006% benzalkonium chloride, and 80% poly (2,2-dioxo-cis/trans-1,4-cyclohexane dimethylene tetrahydrofuran); in FIG. 9 the device comprised 20% tetracycline, 0.05% benzalkonium chloride, and 80% poly(2,2-dioxo-cis/trans-1,4-cyclohexane dimethylene tetrahydrofuran; and in FIG. 10, the device comprised 20% tetracycline, 0.1% benzalkonium chloride, and 80% poly(2,2-dioxo-cis/trans-1,4-cyclohexane dimethylene tetrahydrofuran).

Although the foregoing invention has been described in detail, by way of discussion and by way of illustration of preferred embodiments and examples for the purpose of clarity of understanding the invention, it will be understood that certain changes and modifications may be practiced within the scope and spirit of the invention.

What is claimed is:

1. A device for delivering a beneficial agent at a controlled rate over a prolonged period of time, wherein the device comprises (a) a shaped body sized and adapted for delivering an agent to an environment of use, the body formed of an erodible release rate controlling material, which material comprises a polymer of the formula:

wherein, $R_1$ is a member selected from the group consisting of divalent, trivalent and titravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, alkenyl of 2 to 7 carbons and alkylene of 1 to 10 carbons; cycloalkenylene of 4 to 7 carbons; cycloalkenylene of 4 to 7 carbons substituted with an alkyl of 1 to 7 carbons, an alkoxy of 1 to 7 carbons, an alkenyl of 2 to 7 carbons, and an alkylene of 1 to 7 carbons; arylene of 6 to 12 carbons; arylene of 6 to 12 carbons substituted with an alkyl of 1 to 7 carbons, an alkoxy of 1 to 7 carbons, and an alkenyl of 2 to 7 carbons; $R_2$ and $R_3$ are selected from the group consisting of alkyl of 1 to 7 carbons; alkenyl of 2 to 7 carbons, alkoxy of 1 to 7 carbons; alkylene of 1 to 7 carbons, alkenylene of 2 to 7 carbons; alkyloxy of 1 to 7 carbons; alkenyloxy of 2 to 7 carbons; alkyleneoxy of 1 to 7 carbons; alkenyleneoxy of 2 to 7 carbons; aryloxy of 6 to 12 carbons; aralkyleneoxy of 8 to 12 carbons; aralkenyleneoxy of 8 to 12 carbons; oxa; $OR_1O$ wherein $R_1$ is as defined above; a heterocyclic ring of 5 to 8 carbons and oxygen atoms formed when $R_2$ and $R_3$ are taken together; a heterocyclic ring of 5 to 8 carbon and oxygen atoms substituted with an alkyl of 1 to 7 carbons, an alkoxy of 1 to 7 carbons and an alkenyl of 2 to 7 carbons formed when $R_2$ and $R_3$ are taken together; a fused polycyclic ring of 8 to 12 carbon and oxygen atoms formed when $R_2$ and $R_3$ are taken together; a fused polycylic ring of 8 to 12 carbons and oxygen atoms substituted with an alkyl of 1 to 7 carbons, an alkoxy of 1 to 7 carbons, and an alkenyl of 2 to 7 carbons; wherein at least one of $R_2$ and $R_3$ is selected from the group consisting of alkoxy, alkenyloxy, and $OR_1O$; and $R_2$ and $R_3$ are taken together a member selected from the group of heterocyclic and fused polycyclic rings having at least one oxygen atom in the ring; and wherein n is greater than 10; (b) a beneficial agent in the body; and (c) a surfactant selected from the group consisting of anionic, cationic and nonionic surfactants.

2. A composition of matter comprising a polymer of the general formula:

wherein, $R_1$ is a member selected from the group consisting of a divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, alkenyl of 1 to 7 carbons, and an alkylene of 1 to 10 carbons; cycloalkenylene of 4 to 7 carbons, cycloalkenylene of 4 to 7 carbons substituted with an alkyl of 1 to 7 carbons, an alkoxy of 1 to 7 carbons, an alkenyl of 2 to 7 carbons, and an alkylene of 1 to 7 carbons; arylene of 6 to 12 carbons; arylene of 6 to 12 carbons substituted with an alkyl of 1 to 7 carbons, an alkoxy of 1 to 7 carbons, and an alkenyl of 2 to 7 carbons; $R_2$ and $R_3$ are selected from the group consisting of alkenyl of 2 to 7 carbons; alkoxy of 1 to 7 carbons; alkylene of 1 to 7 carbons; alkenylene of 2 to 7 carbons; alkyleneoxy of 1 to 7 carbons; aryloxy of 6 to 12 carbons; aralkyleneoxy of 8 to 12 carbons; alkenyleneoxyl of 2 to 7 carbons; aralkenyleneoxy of 8 to 12 carbons; $OR_1O$ wherein $R_1$ is as defined; a heterocyclic ring of 5 to 8 carbons and oxygen atoms formed when $R_2$ and $R_3$ are taken together; a heteroxcyclic ring of 5 to 8 carbon and oxygen atoms substituted with an alkyl of 1 to 7 carbons, an alkoxy of 1 to 7 carbons and an alkenyl of 2 to 7 carbons formed when $R_2$ and $R_3$ are taken together; a fused polycyclic ring of 8 to 12 carbon and oxygen atoms formed when $R_2$ and $R_3$ are taken together; a fused polycyclic ring of 8 to 12 carbon and oxygen atoms substituted with an alkyl of 1 to 7 carbons, an alkoxy of 1 to 7 carbons and an alkenyl of 2 to 7 carbons; n is greater than 10; and from 0.001% to 5% by weight of a surfactant selected from the group consisting of anionic, cationic and nonionic surfactants.

3. A device for delivering the beneficial agent at a controlled rate over a prolonged period of time according to claim 1, wherein the anionic surfactant is a member selected from the group consisting of sodium oleate, sodium lauryl sulfate, sodium cetyl sulfate, sodium stearyl sulfate, sodium alkylbenzene sulfonate, dralkyl sulfosuccinate, dioctylester of sodium sulphosuccinic acid; and sodium salt of alkylated aryl polyether sulfate.

4. A device for delivering the beneficial agent at a controlled rate over a prolonged period of time according to claim 1, wherein the cationic surfactant is a member selected from the group consisting of lauryldimethylbenzylammonium chloride, diisobutylphenoxyethoxyethyldimethyl benzylammonium chloride, alkyldimethylbenzylammonium chloride, laurylisoquinolinium bromide, cetylethyldimethylammonium chloride, stearyldimethylbenzylammonium chloride, and ethanolated alkyl guanidine complex.

5. A device for delivering the beneficial agent at a controlled rate over a prolonged period of time according to claim 1, wherein the nonionic surfactant is a member selected from the group consisting of dodecylphenoxypolyethoxyethanol, isooctylphenoxypolyethoxythanol, polyoxyethylene sorbitan mololaurate, polyoxyethylene stearate, polyoxyethylene laurylalcohol and polyglycol ether of alkylphenol.

6. The device for delivering the beneficial agent according to claim 1 wherein the beneficial agent is a member selected from the group consisting of a pesticide, herbicide, germicide, biocide, algicide, fungicide, insecticide and rodenticide.

7. A device for delivering a drug at a controlled rate for a prolonged period of time, wherein the device comprises: (a) a matrix sized, shaped and adpated for delivering a drug to a biological enviornment, the body formed of a bioerodible drug release rate controlling polymer of the formula:

wherein $R_1$ is a member selected from the group consisting of a divalent, trivalent and tetravelent radicals consisting of alkylene of 1 to 10 carbon atoms; alkenylene of 2 to 10 carbon atoms; alkyleneoxy of 2 to 6 carbon atoms; cycloalkylene of 3 to 7 carbon atoms; cycloalkylene of 3 to 7 carbon atoms substituted with an alkyl of 1 to 7 carbon atoms, an akloxy of 1 to 7 carbon atoms, alkenyl of 2 to 7 carbon atoms and an aklylene of 1 to 10 carbon atoms; cycloalkenylene of 4 to 7 carbon atoms; cycloalkenylene of 4 to 7 carbon atoms substituted with an alkyl of 1 to 7 carbon atoms, an alkoxy of 1 to 7 carbon atoms, an alkenyl of 2 to 7 carbon atoms and an alkylene of 1 to 10 carbon atoms; arylene of 6 to 12 carbon atoms; and arylene of 6 to 12 carbons atoms, substituted with an alkyl of 1 to 7 carbon atoms, and alkylene of 1 to 10 carbon atoms, and an alkenyl of 2 to 7 carbon atoms; and wherein $R_2$ and $R_3$ are taken together to form a heterocyclic ring having from 1 to 2 oxygen atoms positioned at $R_2$ and $R_3$ with the ring a member selected from the group consisting of tetrahydrofuranyl, dihydrofuranyl, dihydrofuranyl ocanyl, oxepanyl, dihydrodioxanyl, dioxolanyl, dioxanyl, dioxepanyl, dioxocanyl and dioxonanyl; and n is greater than 10; (b) a drug in the matrix selected rom the group consisting of locally and systemically acting drugs; and (c) a surfactant in the matrix, which surfactant is selected from the group consisting of anionic, nonionic and cationic surfactants.

8. A device for delivering a drug at a controlled rate according to claim 7 wherein the drug is a member selected from the group consisting of gastrointestional, hypnotic, sedative, psychic energizer, tranquilizer, anticonvulsant, antiparkinson, muscle relaxant, analgesic, antipyretic, antiinflammatory, anesthetic, antispasmodic, antimicrobial, antiviral, antiulcer, hormonal, sympathomimetic, duiretic, contraceptive and ophthalmic drugs.

* * * * *